Figure 1:
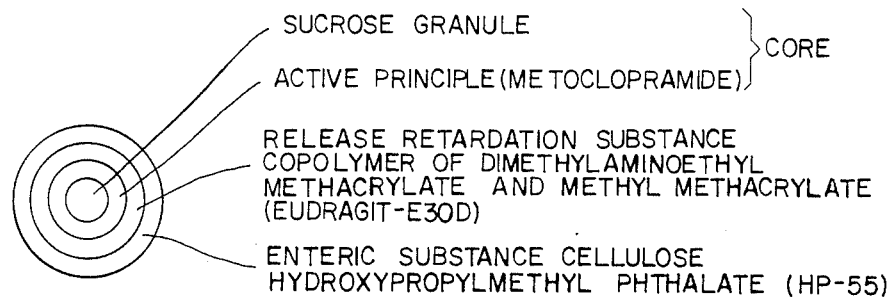

United States Patent [19]

Hata et al.

[11] Patent Number: 4,808,416
[45] Date of Patent: Feb. 28, 1989

[54] PREPARATION OF A SLOW-RELEASE DRUG

[75] Inventors: Takehisa Hata, Kyoto; Hisami Yamaguchi; Satoshi Ueda, both of Hyogo; Masateru Kodani, Osaka, all of Japan

[73] Assignee: Laboratories Delagrange, Paris, France

[21] Appl. No.: 50,765
[22] PCT Filed: Sep. 12, 1986
[86] PCT No.: PCT/FR86/00306
§ 371 Date: Jul. 9, 1987
§ 102(e) Date: Jul. 9, 1987
[87] PCT Pub. No.: WO87/01588
PCT Pub. Date: Mar. 26, 1987

[30] Foreign Application Priority Data

Sep. 12, 1985 [JP] Japan .................. 60-202855

[51] Int. Cl.⁴ ............................... A61K 9/16
[52] U.S. Cl. ..................... 424/497; 424/494
[58] Field of Search ............ 424/471, 497, 494

[56] References Cited

U.S. PATENT DOCUMENTS 4,656,024 4/1987 Leruelle ............... 424/497

FOREIGN PATENT DOCUMENTS 0092060 10/1983 European Pat. Off. .
0148811 7/1985 European Pat. Off. .
1949894 10/1969 Fed. Rep. of Germany .
82/01468 5/1982 France .

Primary Examiner—Michael Lusignan
Attorney, Agent, or Firm—Fitzpatrick, Cella, Harper & Scinto

[57] ABSTRACT

The invention concerns the preparation of a slow-release drug characterized by the coating of a core comprising a therapeutically active principle by means of a substance which retards its release and by means of an additional layer consisting of an enteric substance.

1 Claim, 1 Drawing Sheet

PREPARATION OF A SLOW-RELEASE DRUG

This invention concerns a slow-release preparation of a drug, characterized by the coating of a core comprising an active principle, such as Metoclopramide, first with a substance which retards its release, such as a copolymer of methyl methacrylate and ethyl acrylate (known as EUDRAGIT E30D), cellulose ethyl, etc., and then with an enteric coating such as cellulose hydroxypropylmethyl phthalate (known as HP-55), carboxymethylcellulose, etc.

The diagram of FIG. 1 indicates the structure of the preparation.

The active principle can be used in granule form, as well as deposited around a neutral core, such as a sucrose granule. Coating is then undertaken with one of the substances listed above, capable of retarding the release of the active principle under acid or basic dissolution conditions, so as to assure a constant dissolution of the active principle in the gastrointestinal tract.

The copolymer sold under the name of EUDRAGIT E30D (Röhm Pharma Co.) is the one most suitable for application of the invention.

Finally, external coating of the preparation is undertaken by means of an enteric substance, preferably the cellulose byproduct sold under the name of HP-55 (SHIN-ETSU CHEMICAL CO.).

A working example of the invention is given in order to illustrate the preparation.

Four hundred parts of 32–42 mesh size sucrose granules are coated in a centrifugal granulator with a solution of SHELLAC resin (44 parts) in ethanol (290 parts) containing talc (60 parts). Then the granules are coated with Metoclopramide in a 5 percent aqueous solution of TC-5R brand hydroxypropyl methyl cellulose ether.

The resulting granules (comprising 30 percent by weight of Metoclopramide) are then coated with Eudragit-E30D in a fluidized bed granulator and a solution of HP-55, cellulose hydroxy propylmethyl phthalate, (15 g) in a 50/50 mixture of ethanol and dichloroethane (400 g) is sprayed thereon in order to obtain the Metoclopramide slow-release preparation.

DISSOLUTION TEST (1) Test preparation:
   Sample (I) was prepared according to the example above.
   Sample (II) was prepared as above, except for the coating of HP-55.
(2) Test method:
   (A) Japanese Pharmacopea (10th edition)
       dissolution: method II (bubbling)
       dissolution medium:
          1st fluid (pH 1.2), 900 ml, 37° C., 100 rpm
   (B) Japanese Pharmacopea (10th edition)
       dissolution: method II (bubbling)
       dissolution medium:
          2nd fluid (pH 6.8), 900 ml, 37° C., 100 rpm
(3) Test result:

|  | Method A | | | | | | | |
|---|---|---|---|---|---|---|---|---|
|  | TIME (HOURS) | | | | | | | |
|  | 0.5 | 1 | 2 | 3 | 4 | 6 | 7 | 8 |
| Rate of dissolution (%) of sample (I) | — | 15 | 30 | 40 | 50 | 60 | 65 | 70 |
| Rate of dissolution (%) of sample (II) | 65 | 80 | 85 | 90 | 92 | 95 | 97 | 98 |

|  | Method B | | | | | |
|---|---|---|---|---|---|---|
|  | TIME (HOURS) | | | | | |
|  | 1 | 2 | 3 | 4 | 6 | 8 |
| Rate of dissolution (%) of sample (I) | 32 | 55 | 63 | 72 | 82 | 86 |
| Rate of dissolution (%) of sample (II) | 30 | 53 | 64 | 70 | 80 | 85 |

We claim:

1. Slow-release preparation comprising, in sequence, a core of a granule having deposited thereon metoclopramide; a first shell of a copolymer of ethyl acrylate and methyl methacrylate in an effective amount of ensure uniform dissolution of said metoclopramide upon oral ingestion; and a second shell of an enteric coating of cellulose hydroxypropylmethylphthalate.

* * * * *

UNITED STATES PATENT AND TRADEMARK OFFICE
CERTIFICATE OF CORRECTION

PATENT NO. : 4,808,416

DATED : February 28, 1989

INVENTOR(S) : TAKEHISA HATA, ET AL.

It is certified that error appears in the above-identified patent and that said Letters Patent is hereby corrected as shown below:

ON THE TITLE PAGE,

IN [56] REFERENCES CITED

U.S. PATENT DOCUMENTS, "Leruelle" should read --Laruelle--.

COLUMN 1

Line 4, "of" should read --for--.
Lines 31-32, "EXAMPLE" should be inserted as a heading between lines 31 and 32.

COLUMN 2

Line 41, "of" should read --to--.

Signed and Sealed this

Twenty-second Day of August, 1989

Attest:

DONALD J. QUIGG

Attesting Officer

Commissioner of Patents and Trademarks